United States Patent [19]
Okamoto et al.

[11] Patent Number: 5,545,521
[45] Date of Patent: Aug. 13, 1996

[54] METHOD FOR DETECTING BIOINDIVIDUALS BY USE OF NONNATURAL TYPE NUCLEIC ACID PROBE

[75] Inventors: Tadashi Okamoto, Yokohama; Yoshinori Tomida, Atsugi; Nobuko Yamamoto, Isehara; Masahiro Kawaguchi, Atsugi, all of Japan

[73] Assignee: Canon Kabushiki Kaisha, Tokyo, Japan

[21] Appl. No.: 163,725

[22] Filed: Dec. 9, 1993

[30] Foreign Application Priority Data

Dec. 11, 1992 [JP] Japan .................... 4-331862

[51] Int. Cl.$^6$ .............. C12Q 1/70; C12Q 1/68; C07H 21/04; C12N 15/00
[52] U.S. Cl. .................... 435/5; 435/6; 435/911; 436/94; 436/164; 436/172; 436/800; 536/23.1; 536/23.7; 536/23.72; 536/23.74; 536/24.32; 935/1; 935/5; 935/8; 935/77; 935/78
[58] Field of Search .................... 435/6, 29, 34, 435/91.1; 436/164, 172, 800, 94; 536/23.1, 24.3–24.32, 23.7, 23.72, 23.74; 935/1, 5, 8, 76–78

[56] References Cited

U.S. PATENT DOCUMENTS 4,232,121  11/1980  Gilman, Jr. et al. .................... 435/32
4,544,546  10/1985  Wang et al. .................... 424/7.1
5,248,671  9/1993  Smith .................... 514/44

FOREIGN PATENT DOCUMENTS

WO90/101560  2/1990  WIPO.

OTHER PUBLICATIONS

Yu et al., "Sensitive Detection of RNAs in Single Cells by Flow Cytometry", Nucleic Acids Research, vol. 20, No. 1, pp. 83–88, 1991.

*Primary Examiner*—W. Gary Jones
*Assistant Examiner*—Bradley L. Sisson
*Attorney, Agent, or Firm*—Fitzpatrick, Cella, Harper & Scinto

[57] ABSTRACT

A method for detecting live individuals comprises a step of reacting a sample with a probe having a nonnatural type nucleic acid and a label substance linked with the nucleic acid, which nonnatural type nucleic acid contains a base sequence complementary to a base sequence of a target nucleic acid in the live target individuals to be detected and which probe is able to be incorporated into the live target individuals; and detecting the probe incorporated into the live target individuals by the utilization of the label substance of the probe when the live target individuals are present in the sample. A probe has a nonnatural type nucleic acid and a label substance linked with the nucleic acid, which nonatural type nucleic acid contains a base sequence complementary to a base sequence of a target nucleic acid in a live target individuals to be detected, and the probe is able to be incorporated into the live target individuals.

13 Claims, No Drawings

METHOD FOR DETECTING BIOINDIVIDUALS BY USE OF NONNATURAL TYPE NUCLEIC ACID PROBE

BACKGROUND OF THE INVENTION

1. Field of the Invention

The present invention relates to a method for detecting, distinguishing or counting cells or microorganisms in a live state at a nucleic acid level by the use of a probe comprising a nonnatural type nucleic acid.

2. Related Background Art

In recent years, it has become important to specify, distinguish, detect or count cells, microorganisms or the like (hereinafter referred to as "target individuals") at a gene level, i.e., at a nucleic acid level for the sake of the diagnosis of a hereditary disease based on the variation of a gene, the detection of cancer cells by the expression of a carcinogenic gene or the detection of a genetic recombinant at a research level.

Heretofore, for the detection of the target individuals and for the count of the number of the target individuals, there have been used a light field microscope observation method, a phase difference microscope observation method, a differential interference microscope observation method and so forth. In order to solve the problem that the target individuals are difficult to observe, or in order to more effectively or more highly sensitively detect the target individuals, they have usually been stained with a dyestuff such as Methylene Blue or Safranine, or a fluorescent dyestuff such as Auramine or fluorescein, and then observed by a light field microscope or a fluorescent microscope.

Needless to say in the case that the target individuals are not stained and even in the case where they are all or partially stained, they can be distinguished from other kinds of individuals by observing and evaluating them from the standpoint of morphology, but a difference of genetic variation cannot be distinguished between the same kind of individuals having no difference in morphology. In addition, the dyestuff and the fluorescent dyestuff scarcely permeate the cytoplasmic membrane and the nuclear membrane of the target individuals in a live state (live target individuals), and so it is difficult to detect the live target individuals with the aid of staining.

On the other hand, as a technique for evaluating the target individuals at the gene level or the nucleic acid level, there has been recently carried out a method in which nucleic acid is extracted from the target individuals and then its base sequence is inspected or patterns obtained by cutting the nucleic acid with a restriction enzyme are inspected. However, even according to such a method, it is still impossible to evaluate the target individuals in the live state, while the morphology is maintained. Furthermore, in the test in which the nucleic acid from the target individuals is treated, the series of operations are intricate and a long period of time is inconveniently taken for the detection.

As one technique for solving the problems of the conventional methods, an in situ hybridization method by which the target individuals can be evaluated at the gene level has been researched in recent years, and it has been partially put to practical use [e.g., Nucleic Acid Research, Vol. 20, No. 1, pp. 83–88 (1991)]. Next, the in-situ hybridization method will be briefly described.

(1) A nucleic acid probe having a base sequence which is complementary to a base sequence inherent in a nucleic acid in the target individuals is prepared. This nucleic acid probe has a certain detectable site (label).

(2) The target individuals are killed with methanol or the like, and then fixed.

(3) The nucleic acid probe is hybridized with the nucleic acid of the fixed target individuals in the target individuals (in-situ).

(4) The probe which has not formed a hybrid is washed off.

(5) The hybrid formed in the target individuals is detected by the utilization of the above-mentioned label.

According to this in-situ hybridization method, a step of extracting the nucleic acid from the target individuals can be omitted. In addition, the detection of the target individuals at the gene level or the nucleic acid level is possible, while the morphology is maintained, and the number of the target individuals can also be counted. In this method, the live target individuals are killed, whereby the cytoplasmic membrane and the nuclear membrane are modified to facilitate the passage of the nucleic acid probe through these membranes.

As described above, according to the in-situ hybridization, the target individuals can be distinguished, detected or counted at the nucleic acid level, while maintaining their morphology, which has been impossible by conventional methods. However, there still remains the problem that the target individuals cannot be detected in the live state.

The reasons why the live target individuals cannot be detected by the conventional in-situ hybridization can be summarized as follows:

(1) The nucleic acid portion of the nucleic acid probe is of a natural type regardless of what is obtained from nature or chemically synthesized, and so the hydrophilic nature of a phosphorus portion is strong. Thus, the probe scarcely permeates the cytoplasmic membrane and the nuclear membrane of the live target individuals.

(2) Even if the nucleic acid probe permeates the cytoplasmic membrane and the nuclear membrane, it is degraded by a single-strand nucleic acid degradation enzyme in the live target individuals on occasion. This tendency is larger when the nucleic acid portion of the nucleic acid probe is RNA than when it is DNA.

(3) In the case that the nucleic acid portion of the nucleic acid probe is DNA, even if the nucleic acid probe forms a hybrid together with the target nucleic acid in the live target individuals, the hybrid is degraded by a double-strand nucleic acid degradation enzyme in the live target individuals on occasion.

(4) Some of fluorescent dyestuffs which can usually be used as the label portion of the nucleic acid probe are harmful to the live target individuals, and if such a dyestuff is utilized, the live target individuals die on occasion.

SUMMARY OF THE INVENTION

Thus, an object of the present invention is to provide a method for detecting, distinguishing or counting target individuals in a live state at a nucleic acid level.

The above-mentioned objects can be achieved by the following present invention.

That is, the first aspect of the present invention is directed to a method for detecting live individuals which comprises a step of reacting a sample with a probe having a nonnatural type nucleic acid and a label substance linked with the nucleic acid, the nonnatural type nucleic acid containing a base sequence complementary to a base sequence of a target nucleic acid in the live target individuals to be detected and the probe being able to be incorporated into the live target individuals; and detecting the probe incorporated into the live target individuals by the utilization of the label substance of the probe when the live target individuals are present in the sample.

The second aspect of the present invention is directed to a probe having a nonnatural type nucleic acid and a label substance linked with the nucleic acid, the above-mentioned nonnatural type nucleic acid containing a base sequence complementary to a base sequence of a target nucleic acid in a live target individuals to be detected and the probe being able to be incorporated into the live target individuals.

DESCRIPTION OF THE PREFERRED EMBODIMENTS

The present invention can be utilized to detect various kinds of microorganisms such as cells, viruses, bacteria, Actinomyces, yeast, mold, mushrooms, algae and Protista as live target individuals by suitably selecting the structure of a probe in compliance with its use.

The probe of the present invention possesses a nonnatural type nucleic acid portion having a structure which can be incorporated into the live target individuals and which is scarcely degraded with a degradation enzyme in the live target individuals. As described above, if the nucleic acid portion of the probe is of a natural type, the probe scarcely permeates a cytoplasmic membrane and a nuclear membrane, and it is liable to be degraded in the live target individuals.

In the present invention, the natural type nucleic acid, in the case of DNA, means nucleic acid in which 2'-deoxyribonucleotides are bonded to each other via a 3'→5' phosphodiester bond. In the case of RNA, it means nucleic acid in which ribonucleotides are bonded to each other via a 3'→5' phosphodiester bond.

In the present invention, the nucleic acid having a structure other than the natural type is fundamentally called the nonnatural nucleic acid. In a living body, the nucleic acid other than the natural type is present in a slight amount, and this kind of nucleic acid is called a modified type and it is in the category of the nonnatural type nucleic acid.

This nonnatural type nucleic acid can be obtained by suitably modifying the nucleic acid having the base sequence necessary for the probe so that the above-mentioned function may be imparted thereto. No particular restriction is put on the method of such a modification, but there can be utilized a method which comprises modifying a phosphoric acid portion, a saccharide portion, a base portion or the like of the nucleic acid in compliance with a purpose. For example, in order to modify the saccharide portion of the nucleic acid, there can be utilized a method which comprises replacing a β-D-ribofuranosyl ring with an anomer or an arabinose ring.

In modifying the nucleic acid, care should be taken so that the function as the probe of the nucleic acid, i.e., the function of forming a hybrid with the target nucleic acid may not be impaired. Specifically, it is preferable that for example, the 5-position of uracil, the 2'-position of the β-D-ribofuranosyl ring or the phosphoric acid portion is modified, the modification of the hydrogen bond site of the base portion being avoided.

Furthermore, the modification of the nucleic acid portion must be selected in consideration of the reaction of the probe with the live target individuals, the incorporation of the probe into the live target individuals and the transportation manner of the probe in the live target individuals. For example, in order to bring the probe into contact with the live target individuals in a suitable buffer solution, the probe is required to be water-soluble. However, from the viewpoint of the incorporation of the probe into the live target individuals, the hydrophilic nature of the probe must be suitably controlled, judging from the fact that the reason why the natural type nucleic acid can scarcely pass through a cytoplasmic membrane and a nuclear membrane is that the hydrophilic nature of the phosphoric acid portion in the nucleic acid is so strong that the phosphoric acid portion can scarcely pass through the hydrophobic structure portion of lipid double membranes of the cytoplasmic membrane and the nuclear membrane. To the contrary, if the nucleic acid is made hydrophobic, its passage through the hydrophilic structure portion of the above-mentioned lipid double membranes is difficult and the water-solubility is also lost. Therefore, it is necessary to control the balance between the hydrophilic portion and the hydrophobic portion in the nucleic acid portion of the probe in compliance with this purpose. This balance between the hydrophilic portion and the hydrophobic portion can be controlled by modifying the phosphoric acid portion to make it hydrophobic, or by introducing a hydrophilic or a hydrophobic functional group into another portion, if necessary.

Furthermore, the modification Should be selected so that the modified probe may be harmless to the live target individuals, and for example, a modification such as the substitution of the 5-position of uracil by fluorine is not preferable.

In the present invention, no particular restriction is put on the labeling of the probe, so long as it permits the detection of the target individuals in the live state, but a dyestuff or a fluorescent dyestuff can be utilized. In selecting the label, for example, the following points should be taken into consideration:

(A) Like the nucleic acid portion, the label portion is also required to be harmless to the live target individuals, and for example, cyanine dyestuffs, azulene dyestuffs and pyrylium dyestuffs which are harmless to the living body can be utilized.

(B) When the fluorescent dyestuff is utilized, it is preferable to select the fluorescent dyestuff having an excitation wave length which has no influence on the detection of the absorption or fluorescence of excitation light by a substance other than the label or which does not give rise to such a problem, in order to avoid the deterioration of a detection sensitivity due to the rise of background attributed to the absorption or fluorescence of excitation light by the live target individuals themselves or a substance present in a detection system. Such a preferable fluorescent dyestuff has the absorption or fluorescence in a near infrared wave length region of from 600 to 1,000 nm. In this connection, it is not preferable to employ, as the label, the dyestuff having the absorption in a wave length region in excess of 1,000 nm, because such a dyestuff tends to generate heat by the absorption. Most of the above-mentioned cyanine dyestuffs, azulene dyestuffs and pyrylium dyestuffs have the absorption and fluorescence in the wave length region of from 600 to 1,000 nm, and this is the reason why the employment of these dyestuffs is advantageous.

In the present invention, when the probe which is incorporated into the live target individuals to form a hybrid with the target nucleic acid is not distinguished from the unreacted probe, the so-called washing operation is necessary. This operation can be achieved by repeating several times a cultivation for 6 to 12 hours in a culture medium containing no probe.

Furthermore, if there is utilized the label which carries out a specific interaction with the double-strand structure of the hybrid and which becomes detectable at the time of the formation of the hybrid with the probe, the above-mentioned washing operation is not necessary, which is advantageous. As such a label, for example, a fluorescent dyestuff such as acridine can be utilized which has a function as an intercalater to the bases of the nucleic acid and which intercalates the double-strand structure to increase a fluorescent intensity.

A method for detecting the live target individuals having the hybrid of the probe and the target nucleic acid can be selected in consideration of the label linked with the probe. When the fluorescent dyestuff is utilized as the label, a flow cytometry method is advantageous, because this method can effectively distinguish the live target individuals from a large amount of the live individuals which are not the target. In this case, if the dyestuff having the absorption and fluorescence in a near infrared wave length region of from 600 to 1,000 nm is used, a small-sized inexpensive laser device such as a semiconductor laser device or an He—Ne laser device can be advantageously utilized as a light source of a flow cytometer (FCM). The live target individuals can be labeled with the probe, and FCM can be utilized for its detection, whereby, for example, the live target individuals extracted from a living body or an environment such as a soil can be rapidly detected, and the number of them can be counted.

No particular restriction is put on the selection of the target nucleic acid of the live target individuals, and so the target nucleic acid can be suitably selected in compliance with a detection purpose. Examples of the utilizable target nucleic acid include genome DNA, ribosome DNA, messenger RNA, plasmid DNA and phage DNA. If the target nucleic acid is present in the form of a large number of copies in one live target individual, measurement can be carried out with a higher sensitivity. Therefore, from this viewpoint, ribosome RNA and messenger RNA are preferable. When the live target individuals are bacteria, plasmid DNA or phage DNA is preferable. In the case that the live target individuals are recombinants into which an extraneous gene is introduced, the extraneous gene, RNA formed therefrom or the like can be utilized as the target nucleic acid, so that the detection of the recombinants can be carried out by the method of the present invention.

Next, the present invention will be described in detail in reference to examples, but the scope of the present invention should not be limited to these examples.

EXAMPLE 1

(1) Synthesis of phosphorothioate type nonnatural type nucleic acid (DNA)

By the use of a DNA automatic synthesizer (trade name 381A, made by ABI Co., Ltd.), there was synthesized a 20-mer all phosphorothioate type oligonucleotide having the following base sequence which was complementary to a portion of a base sequence of β-actin mRNA of HeLa cells:

5'GCGCGGCGATATCATCATTC3' where the underlined portion was a digesting site by the restriction enzyme EcoRV. Then, amino-modifier (C6) (manufactured by Gren Research Co., Ltd.) was bonded to the 5' terminal of this oligonucleotide by the automatic synthesizer.

(2) Succinimido esterification of cyanine dyestuff

Under an argon gas stream, 0.5 g of a cyanine dyestuff (trade name NK-3669, made by Nippon Kanko Shikiso Co., Ltd.) having a carboxyl group was dissolved in 30 ml dry DMF in a 100 ml shaded reactor. Afterward, the solution was cooled to −10° C., and 0.4 g N,N'-disuccinimidyl carbonate was then added thereto. Next, reaction was carried out at the same temperature for 5 hours, and the reaction solution was then poured into 150 ml chloroform, washed with 200 ml a sodium chloride solution three times, and then washed with water. Afterward, the used solvent was distilled off. The resulting residue was purified through a silica gel column, and then crystallized in ethanol-isopropyl ether to obtain 0.2 g a crystalline succinimido ester of the cyanine dyestuff.

(3) Linkage of nonnatural type oligonucleotide with cyanine dyestuff 0.1 μm the all phosphorothioate type oligonucleotide synthesized in the preceding paragraph (1) was dissolved in 700 μl water. Next, a 1M sodium carbonate buffer solution (pH=9.0) was added to the solution, and 200 μl a DMF solution containing 1 mg succinimido ester of the cyanine dyestuff synthesized in the preceding paragraph (2) was then slowly added to the solution with stirring. Afterward, reaction was carried out at 40° C. for 24 hours. Next, the excessive dyestuff was removed from the resulting reaction solution by means of a gel filtration column NAP-25, followed by purification with RPLC, to obtain 75 nmol a phosphorothioate type oligonucleotide linked with the cyanine dyestuff. This nucleotide was used as a probe (I) in a subsequent operation.

(4) Digestion with enzyme 100 pmol the probe (I) was subjected to digestion reaction for 1 hour with S1 nuclease in accordance with a predetermined protocol. As a result of a polyacrylamide electrophoresis (PAGE) of the reaction solution, it was apparent that the probe (I) was not digested with S1 nuclease. Next, a natural type oligonucleotide (i) which was complementary to the probe (I) was synthesized by the use of a DNA automatic synthesizer (trade name 381A, made by ABI Co., Ltd.), and the thus synthesized natural type oligonucleotide (i) was hybridized with the probe (I) to obtain a hybrid. Afterward, this hybrid was subjected to digestion reaction for 1 hour with the restriction enzyme EcoRV in accordance with a predetermined protocol. After completion of the reaction, PAGE of the reaction solution was carried out, and as a result, it was apparent that this hybrid could not be cut with EcoRV.

(5) Hybridization

After Hela cells were suspended in an MEM culture medium, dishes were inoculated with them so as to be $2.5 \times 10^5$/dish. These cells were cultured at 37° C. for 36 hours, further successively cultured for 24 hours in an MEM culture medium containing the probe (I) at a concentration of 10 nM, and then cultured for 12 hours in an MEM culture medium containing no probe (I) twice. The obtained culture medium was washed with PBS (−) twice, treated with PBS (−) containing 0,001% trypsin and 1 mM EDTA, and then centrifugally separated to collect the cells. The thus collected cells were suspended in PBS (−), and the resulting cell suspension was used for measurement by FCM in the following paragraph (6).

(6) Measurement by FCM

FCM which was used herein was equipped with a semiconductor laser having a wave length of 780 nm as a light source, and in the measurement of fluorescence, a filter was used which could transmit 90% or more of a fluorescent wave length of 830 nm of the cyanine dyestuff label in the probe (I).

In the first place, the untreated HeLa cells (untreated cells) which were not treated with the probe (I) were previously measured by FCM to inspect the pattern of forward scatter. According to the measurement of the fluorescence, any untreated HeLa cells having the fluorescence were not detected.

Next, the suspension of the cells treated with the probe (I) in the preceding paragraph (5) was subjected to the measurement. As a result, the measured pattern of the forward scatter was the same as in the above-mentioned untreated cells. About 95% of the fine particles (the number of the measured particles =5,000 inclusive of the cells) having the measured forward scatter was gathered in the main peak. Therefore, the residue occupying 5% of the fine particles was dust and the like contained in the buffer solution. About 90% of the cells constituting the main peak had the fluorescence. Judging from the results of undermentioned Comparative Examples 1 and 2, this result indicates that the nonnatural type probe (I) specifically forms a hybrid with the label nucleic acid in the HeLa cells. As is apparent from the foregoing, by employing the probe labeled with the fluorescent dyestuff which probe is comprised of the nonnatural type nucleic acid having the structure capable of being incorporated by the live cells, the cells can be detected in the live state, and the number of the cells can also be counted.

COMPARATIVE EXAMPLE 1

An all phosphorothioate type 20-mer deoxyadenylic homooligonucleotide (which was of a nonnatural type and which was different from the probe (I) of Example 1 in a base sequence) was synthesized by the use of a DNA automatic synthesizer (trade name 381A, made by ABI Co., Ltd.), and this deoxyadenylic homooligonucleotide was linked with a cyanine dyestuff by the same procedure as in Example 1 to obtain a probe (II). Next, the treatment of HeLa cells was carried out in the same manner as in Example 1 by the use of this probe (II), and measurement was done by FCM. As a result, only about 1% of fluorescence measured in Example 1 was detected.

COMPARATIVE EXAMPLE 2

An all phosphoric diester (natural) type 20-mer oligonucleotide having the same base sequence as in the probe (I) of Example 1 was synthesized by the use of a DNA automatic synthesizer (trade name 381A, made by ABI Co., Ltd.), and this oligonucleotide was then linked with a cyanine dyestuff by the same procedure as in Example 1 to obtain a probe (III). Next, the treatment of HeLa cells was carried out in the same manner as in Example 1 by the use of this probe (III), and measurement was done by FCM. As a result, no fluorescence was detected.

EXAMPLE 2

(1) Synthesis of nucleic acid probe

An all phosphorothioate type 20-mer nonnatural type oligonucleotide having the same base sequence as in the probe (I) of Example 1 was synthesized by the use of a DNA automatic synthesizer (trade name 381A, made by ABI Co., Ltd.), and a thiol modifier (C6) (made by Gren Research Co., Ltd.) was then condensed at the 5' terminal of the oligonucleotide by the automatic synthesizer. Cleaving from a CPG column, removing a protective group, removing trityl and purification by RPLC were carried out in accordance with a predetermined protocol. Next, N-(9-acridinyl)maleimide (made by Sigma Co., Ltd.) was bonded to the resulting oligonucleotide in which the thiol group was bonded to the 5' terminal, whereby a probe (IV) was obtained. The bonding conditions were the same as in the case of the bonding of a cyanine dyestuff in Example 1 except that a 1M sodium phosphate buffer solution (pH=7.0) was used. The acridine portion which was the label portion of this probe (IV) was an intercalater to the base pair of a double-strand nucleic acid.

In addition to the above-mentioned probe (IV), FITC (fluorescein isothiocyanate, made by Sigma Co., Ltd.) was bonded to the 5' terminal of the all phosphorothioate type 20-mer nonnatural type oligonucleotide through hexanolamine linker in the same manner as described in Example 1 to obtain a probe (V). Incidentally, this FITC was not an intercalater to the base pair of a nucleic acid.

(2) Digestion with enzyme

A test was conducted to determine whether or not the probes (IV) and (V) were digested with S1 nuclease by the same procedure as in Example 1, and as a result, it was apparent that they were not digested. Furthermore, a natural type oligonuleotide (ii) having a base sequence which was complementary to the probes (IV) and (V) was synthesized by the same procedure as in Example 1, and a hybrid of the probe (IV) and the oligonuleotide (ii) as well as a hybrid of the probe (V) and the oligonucleotide (ii) were separately formed. Next, a test was ran to see whether or not these probes (IV) and (V) were digested with EcoRV, and as a result, it was apparent that they were not digested.

(3) Hybridization

A hybridization treatment of HeLa cells was carried out in the same manner as in Example 1 by the use of each of the probe (IV) and (V). In this case, the final culture time in a culture medium containing no probe was set to 0 hour, 12 hours and 24 hours to prepare samples which underwent the different culture times.

(4) Measurement by FCM

FCM which was used herein was equipped with an argon laser. Furthermore, each measurement was made for 5,000 HeLa cells. Table 1 shows the variation of fluorescent intensity ratios corresponding to the culture times in the final culture of the HeLa cells treated with the probes (IV) and (V) respectively which were obtained by fluorescent measurement with FCM (each of these ratios was a ratio of the fluorescent intensity of each sample to that of the standard sample in which the final culture time in the culture medium containing no probe is 0 hour, and in this case, the fluorescent intensity of the standard sample was regarded as 1.0).

TABLE 1

| Probe | Final Culture Time in Culture Medium Containing No Probe | | |
|---|---|---|---|
| | 0 hour | 12 hours | 24 hours |
| IV | 1.0 | 0.92 | 0.91 |
| V | 1.0 | 0.55 | 0.51 |

It can be understood from the results in Table 1 that when acridine which was the fluorescent dyestuff as the intercalater was used as the label, the hybrid of the target nucleic acid and the probe can be maintained more stably, and so a more stable measurement can be carried out.

According to the present invention, a probe comprising a nonnatural type nucleic acid is used, whereby target individuals can be detected, distinguished or counted in a live state at a nucleic acid level. In addition, a label to be bonded to the probe functioning as an intercalater to the base pair of a nucleic acid is used, whereby a more stable measurement is possible.

What is claimed is:

1. A method for detecting live target individuals which comprises a step of reacting a sample with a probe having a nonnatural type nucleic acid and a label substance linked with said nucleic acid, said nonnatural type nucleic acid containing a base sequence complementary to a base sequence of a target nucleic acid in the live target individuals to be detected and said probe being able to be incorporated into said live target individuals wherein said labeled probe is harmless to said live target individuals; and detecting said labeled probe incorporated into said live target individuals by the utilizations of said label substance of said probe when said live target individuals are present in said sample.

2. The method for detecting live target individuals according to claim 1 wherein said probe is water-soluble.

3. The method for detecting live target individuals according to claim 1 wherein said probe has a structure which can easily pass through a cytoplasmic membrane or a nuclear membrane.

4. The method for detecting live target individuals according to claim 1 wherein said probe has a structure which is not degraded with a nucleic acid degradation enzyme.

5. The method for detecting live target individuals according to claim 1 wherein said label substance is a dyestuff.

6. The method for detecting live target individuals according to claim 5 wherein said dyestuff is a fluorescent dyestuff.

7. The method for detecting live target individuals according to claim 6 wherein said fluorescent dyestuff has absorption and fluorescence in a near infrared wave length region of from 600 to 1,000 nm.

8. The method for detecting live target individuals according to claim 6 or 7 wherein said fluorescent dyestuff is an intercalater to the base pair of said nucleic acid.

9. The method for detecting live target individuals according to claims 6 or 7 wherein the detection of said fluorescent dyestuff is carried out by means of a flow cytometry.

10. The method for detecting live target individuals according to claim 1 wherein said target nucleic acid is a Genome DNA.

11. The method for detecting live target individuals according to claim 1 wherein said target nucleic acid is a ribosome RNA.

12. The method for detecting live target individuals according to claim 1 wherein said target nucleic acid is a messenger RNA.

13. A method for detecting live target individuals comprising:

Providing a probe comprising a nonnatural type single-stranded nucleic acid to which a labeling substance is attached; wherein the nonnatural type single-stranded nucleic acid has a base sequence complementary to a base sequence of a single-stranded nucleic acid in the live target individuals, which is unique to the live target individuals and wherein said labeled probe is harmless to said live target individuals;

adding the labeled probe to a sample to be tested for presence of the live target individuals to incorporate the probe into the live target individuals; and detecting the probe incorporated into the live target individuals by measuring the labeling substance of the probe.

* * * * *